United States Patent [19]
Bell

[11] Patent Number: 5,579,785
[45] Date of Patent: Dec. 3, 1996

[54] CPR SAFETY DEVICE

[76] Inventor: Bruce W. Bell, 318 E. 15th St.; apt. 6E, New York, N.Y. 10003

[21] Appl. No.: 500,472

[22] Filed: Jul. 10, 1995

[51] Int. Cl.⁶ .................................................. A61F 5/37
[52] U.S. Cl. ..................... 128/875; 128/876; 280/801.1
[58] Field of Search .................................. 128/845, 846, 128/869, 874, 875, 876; 280/748, 801

[56] References Cited

U.S. PATENT DOCUMENTS

| | | | |
|---|---|---|---|
| 3,524,679 | 8/1970 | Lavenne | 280/748 |
| 4,251,100 | 2/1981 | Rolandelli | 280/801 |
| 4,563,023 | 1/1986 | Clarkson | 280/748 |
| 4,632,425 | 12/1986 | Barratt | 280/801 |
| 5,256,135 | 10/1993 | Avihod | 602/19 |

*Primary Examiner*—Michael A. Brown
*Attorney, Agent, or Firm*—Michael I. Kroll

[57] ABSTRACT

A CPR safety device which comprises a harness/vest worn about a torso of an emergency medical technician. A facility is for securing the harness/vest within a compartment of an ambulance. The emergency medical technician can safely administer continuous CPR to a patient on a stretcher in the compartment, while the patient is being transported by the ambulance.

2 Claims, 4 Drawing Sheets

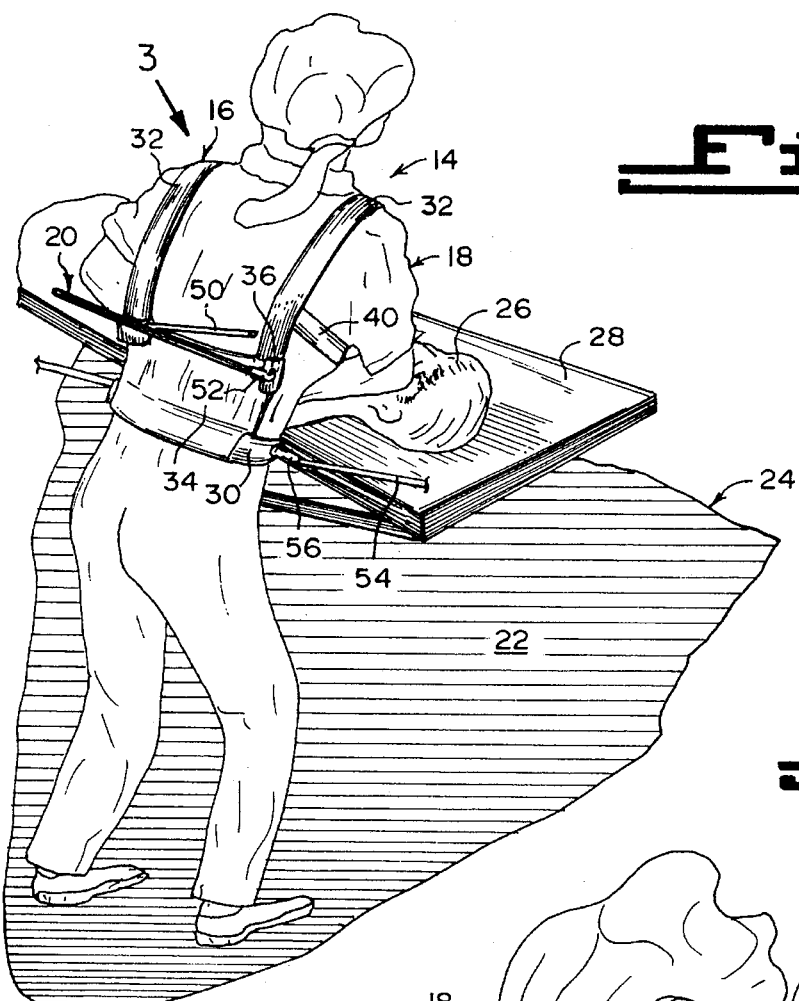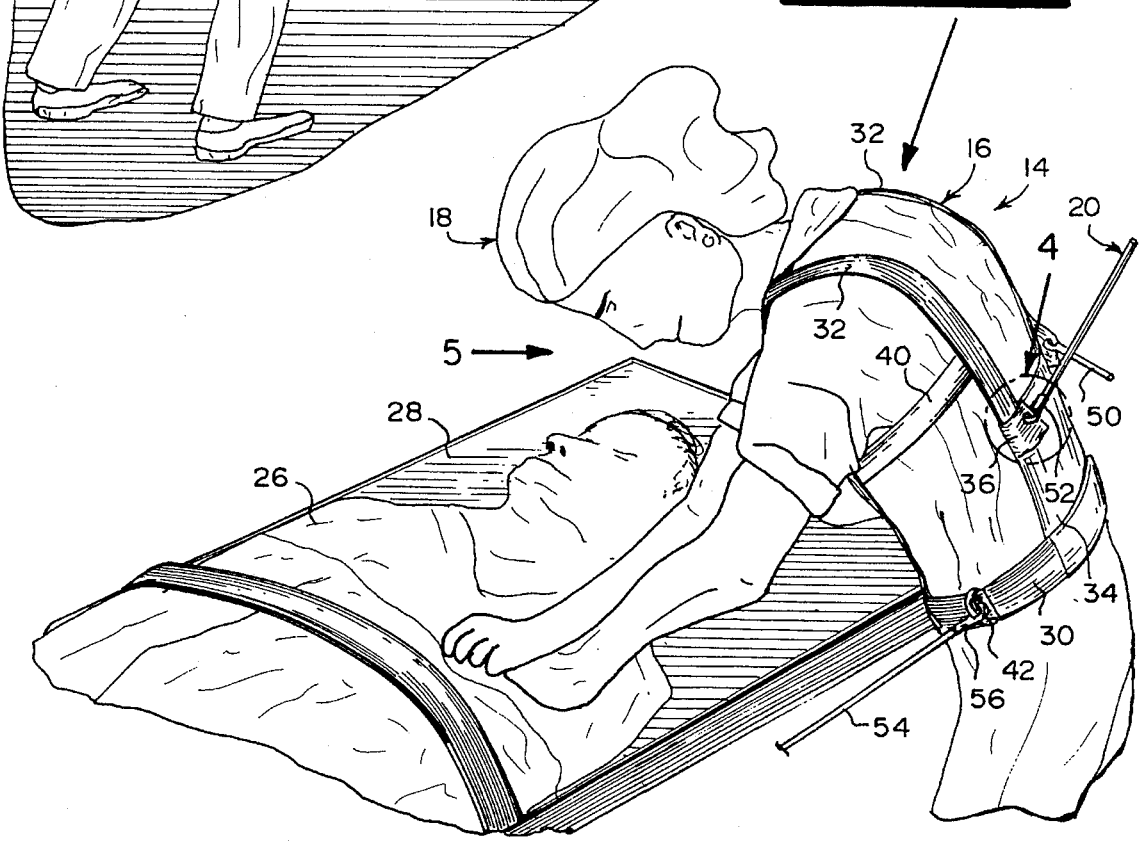

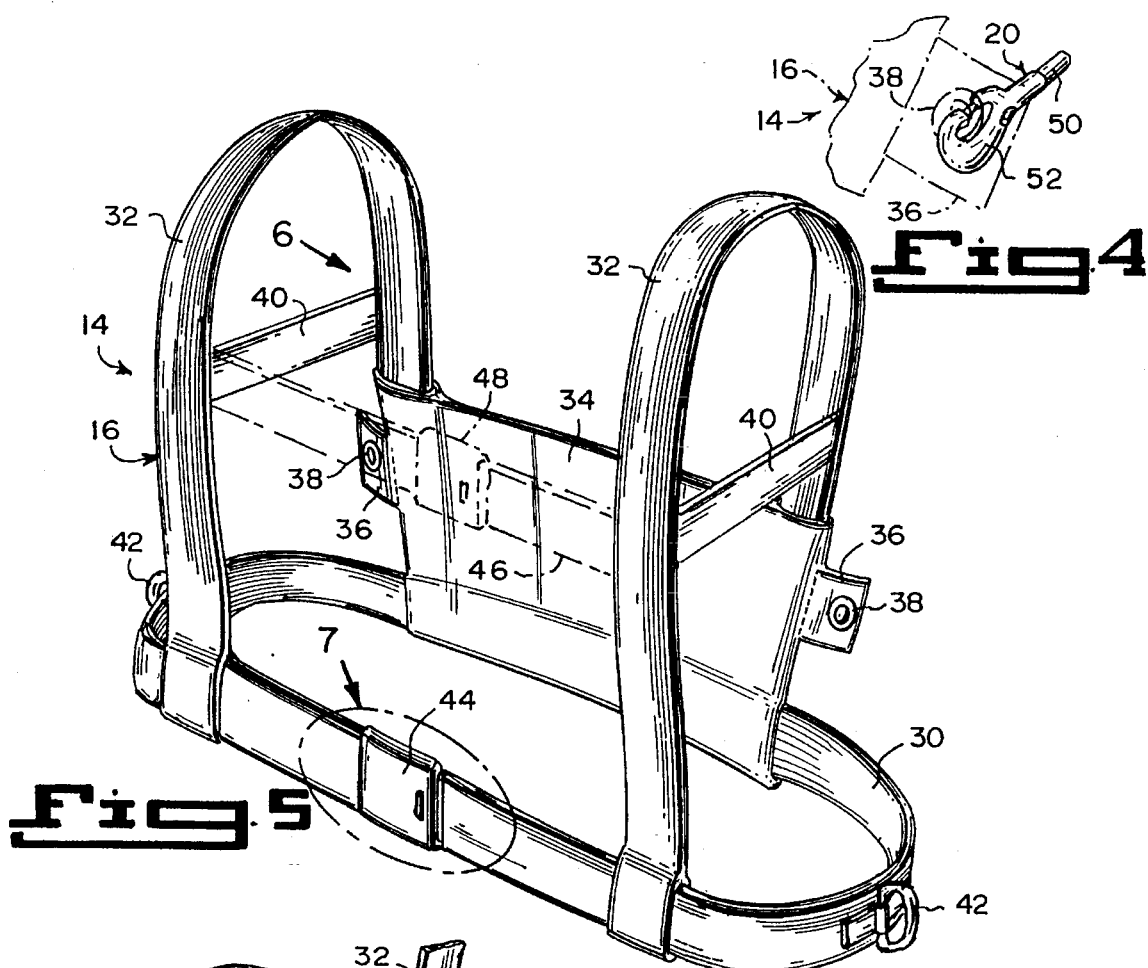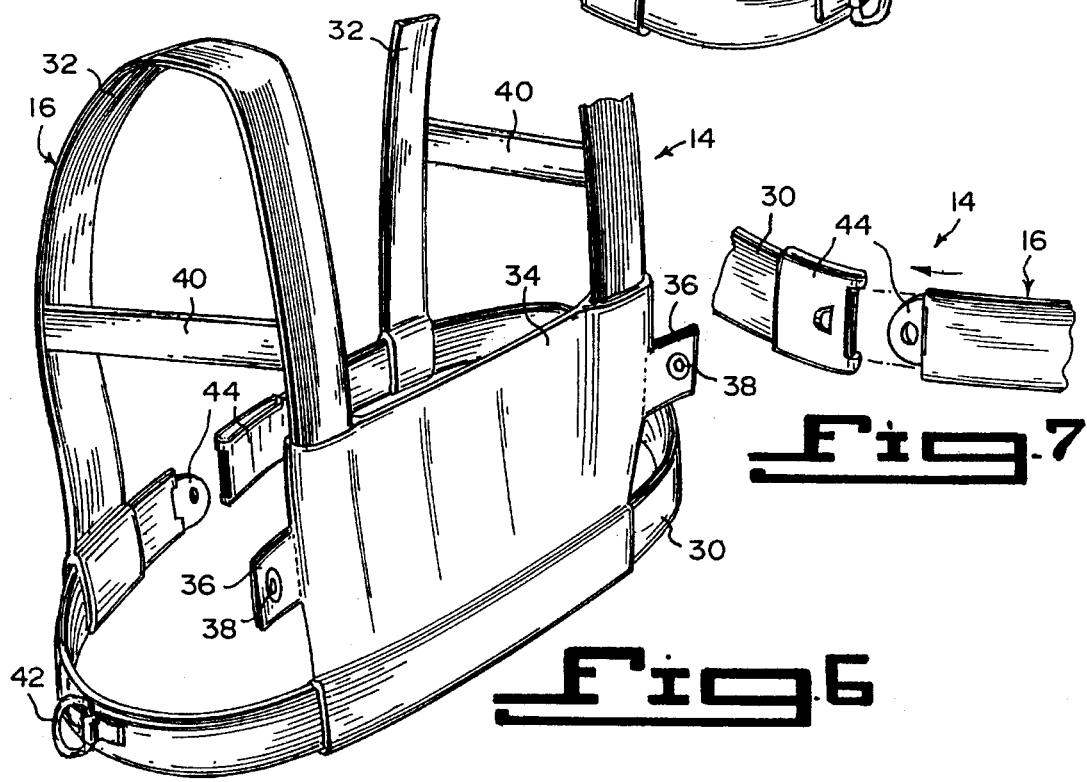

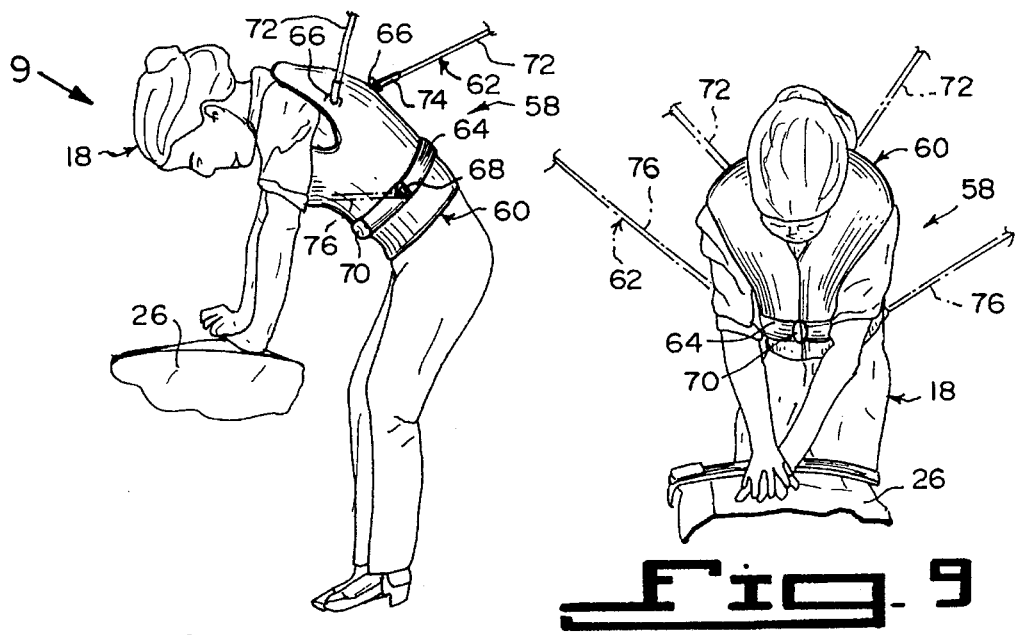
Fig. 8
Fig. 9
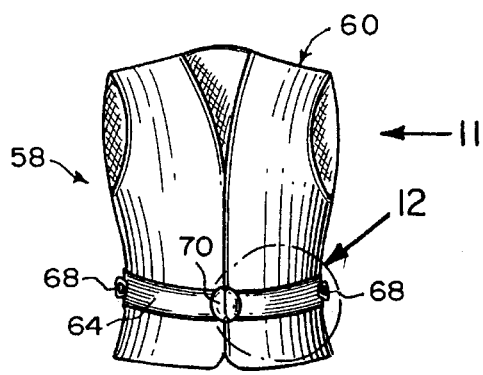
Fig. 10
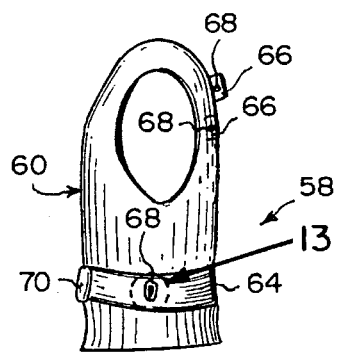
Fig. 11
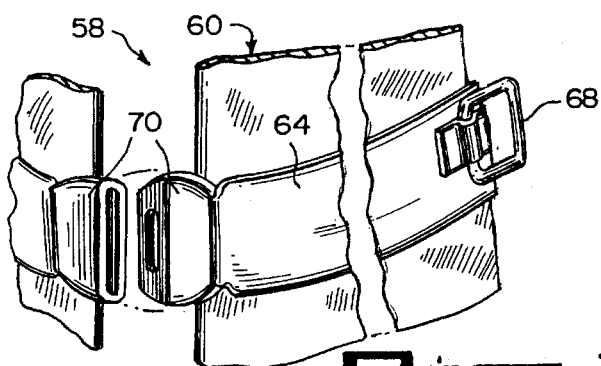
Fig. 12
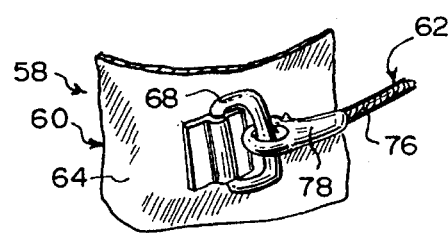
Fig. 13

5,579,785

CPR SAFETY DEVICE

BACKGROUND OF THE INVENTION

1. Field of the Invention

The instant invention relates generally to safety harnesses and more specifically it relates to a CPR safety device.

2. Description of the Prior Art

Numerous safety harnesses have been provided in prior art that are adapted to be worn by window washers, bunji-cord jumpers, race car drivers, boaters, military helicopter personal, mountain climbers, parachutists, so as to protect them from danger. While these units may be suitable for the particular purpose to which they address, they would not be as suitable for the purposes of the present invention as heretofore described.

SUMMARY OF THE INVENTION

About 800,000 Americans die of heart attacks every year. Most of these deaths occur before the victims can get to a hospital, and physicians believe that many deaths could be prevented with the proper use of a three-part method for life support called CPR, for cardiopulmonary resuscitation, or heart (cardio) and lung (pulmonary) revival. The first part of CPR, clearing the airways, and the second part, mouth-to-mouth resuscitation, or artificial respiration, are easy to learn and are very useful for many other life-threatening emergencies. But the third part of CPR, external heart massage, must be studied carefully and practiced in advance to be sure of using it properly and safely.

A primary object of the present invention is to provide a CPR safety device that will overcome the shortcomings of the prior art devices.

Another object is to provide a CPR safety device being a harness or vest worn by an emergency medical technician that is secured within an ambulance, so as to stabilize the emergency medical patient while transporting the patient in the ambulance.

An additional object is to provide a CPR safety device that will also increase the likelihood of patient viability, by allowing the emergency medical technician to safety perform uninterrupted CPR to the patient in the ambulance while it is moving.

A further object is to provide a CPR safety device that is simple and easy to use.

A still further object is to provide a CPR safety device that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views, and wherein;

FIG. 2 is a perspective view taken in the direction of arrow 2 in FIG. 1.

FIG. 3 is a perspective view taken in the direction of arrow 3 in FIG. 2.

FIG. 4 is a perspective view of the area indicated by arrow 4 in FIG. 3, showing one safety line hook fastener connected to one of the stabilizing tabs that is in phantom.

FIG. 5 is a front perspective view of the first embodiment per se.

FIG. 6 is a rear perspective view with parts broken away as indicated by arrow 6 in FIG. 5.

FIG. 7 is a front perspective view of the area indicated by arrow 7 in FIG. 5, showing the quick release retracting buckle opened.

FIG. 8 is a side perspective view of a second embodiment of the instant invention, being worn on an emergency medical technician.

FIG. 9 is a front perspective view taken in the direction of arrow 9 in FIG. 8.

FIG. 10 is a front perspective view of the second embodiment per se.

FIG. 11 is a side perspective view taken in the direction of arrow 11 in FIG. 10.

FIG. 12 is an enlarged perspective view of the area indicated by arrow 12 in FIG. 10, showing the quick release retracting buckle opened.

FIG. 13 is an enlarged perspective view of the area indicated by arrow 13 in FIG. 11, showing one safety line hook fastener connected to one of the D-ring attachments.

Similar reference characters denote corresponding features consistently throughout the attached drawings.

DETAILED DESCRIPTION OF THE PREFERRED EMBODIMENTS

Figure 1:
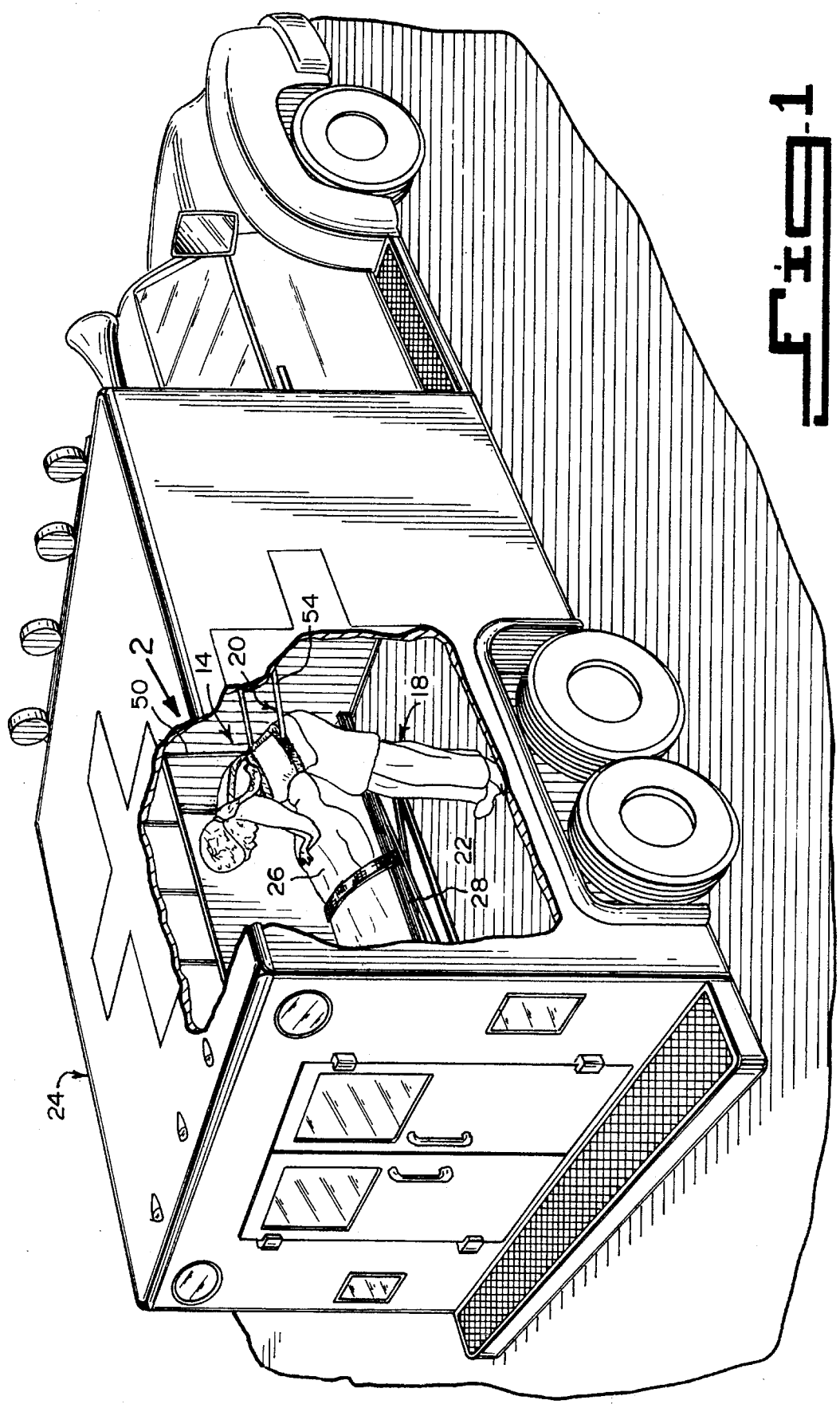
FIG. 1 is a perspective view of an ambulance with parts broken away, showing an emergency medical technician wearing a first embodiment of the instant invention.

Turning now descriptively to the drawings, in which similar reference characters denote similar elements throughout the several views, FIGS. 1 through 7 illustrate a CPR safety device 14, which comprises a harness 16 worn about a torso of an emergency medical technician 18. A facility 20 is for securing the harness 16 within a compartment 22 of an ambulance 24. The emergency medical technician 18 can safely administer continuous CPR to a patient 26 on a stretcher 28 in the compartment 22, while the patient 28 is being transported by the ambulance 24.

The harness 16 includes a belt 30, to extend around a waist of the emergency medical technician 18. A pair of shoulder straps 32 extend upwardly from the belt 30. A back separator panel 34 extends between the shoulder straps 32. A pair of stabilizing tabs 36 are provided. Each stabilizing tab 36 is located on one side of the back separator panel 34. Each stabilizing tab 36 also includes an eyelet 38 therein.

The harness 16 further contains a pair of lateral underarm support straps 40. Each lateral underarm support strap 40 extends between one shoulder strap 32. The belt 30 includes a pair of D-ring attachments 42. Each D-ring attachment 42 is affixed mid-lateral onto the belt 30.

The belt 30 further contains a quick release retracting buckle 44, so that the emergency medical technician 18 can easily put on and take off the harness 16. A shown in FIG. 5 in phantom in FIG. 5, the harness 16 can further include a chest strap 46 extending between the shoulder straps 32. A second quick release retracting buckle 48 is on the chest strap 46, to help the emergency medical technician 18 to easily put on and take off the harness 16.

The securing facility 20 consists of a pair of safety lines 50. Each safety line 50 is affixed to a first end to a wall surface in the compartment 22 of the ambulance 24. A pair of hook fasteners 52 are provided. Each hook fastener 52 is attached to a second end of one safety line 50. Each hook fastener 52 can connect to one eyelet 38 in one stabilizing tab 36.

The securing facility 20 further includes a second pair of safety lines 54. Each safety line 54 is affixed at a first end to teh stretcher 28. A second pair of hook fasteners 56 are also provided. Each hook fastener 56 is attached to a second end of one safety line 54. Each hook fastener 56 can connect to one D-ring attachment 42 on the belt 30.

A modified CPR safety device 58 is shown in FIGS. 8 through 13, which comprises a vest 60 worn about the torso of the emergency medical technician 18. A facility 62 is for securing the vest 60 within the compartment 22 of the ambulance 24. The emergency medical technician 18 can safely administer continuous CPR to the patient 26 on the stretcher 28 in the compartment 22, while the patient 26 is being transported by the ambulance 24.

The vest 60 includes a belt 64 to extend around a waist of the emergency medical technician 18. The vest 60 further contains a pair of support tabs 66. Each support tab 66 is located on an upper lateral back portion of the vest 60. Each support tab 66 includes an eyelet 68 therein.

The belt 64 contains a pair of D-ring attachments 68. Each D-ring attachment 68 is affixed mid-lateral onto the belt 64. The belt 64 further includes a quick release retracting buckle 70, so that the emergency medical technician 18 can easily put on and take off the vest 60.

The securing facility 62 consists of a pair of safety lines 72. Each safety line 72 is affixed at a first end to the wall surface in the compartment 22 of the ambulance 24. A pair of hook fasteners 74 are provided. Each hook fastener 74 is attached to a second end of one safety line 72. Each hook fastener 72 can connect to one eyelet 68 in one support tab 66.

The securing facility 62 further includes a second pair of safety lines 76. Each safety line 76 is affixed at a first end to the wall surface in the compartment 22 of the ambulance 24. A second pair of hook fasteners 78 are also provided. Each hook fastener 78 is attached to a second end of one safety line 76. Each hook fastener 78 can connect t one D-ring attachment 68 on the belt 64.

LIST OF REFERENCE NUMBERS

14 CPR safety device
16 harness of 14
18 emergency medical technician
20 securing facility of 14
22 compartment in 24
24 ambulance
26 patient on 28
28 stretcher in 22
30 belt of 16
32 shoulder strap of 16
34 back separator panel of 16
36 stabilizing tab on 34
38 eyelet in 36
40 underarm support strap of 16
42 D-ring attachment on 30
44 quick release retracting buckle on 30
46 chest strap on 16
48 second quick release retracting buckle on 46
50 safety line of 20
52 hook fastener of 20
54 safety line of 20
56 hook fastener of 20
58 modified CPR safety device
60 vest of 58
62 securing facility of 58
64 belt of 60
66 support tab on 60
68 eyelet in 66
68 D-ring attachment on 64
70 quick release retracting buckle on 64
72 safety line of 62
74 hook fastener of 62
76 safety line of 62
78 hook fastener of 62

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A CPR safety device which comprises:

a) a harness worn about a torso of an emergency medical technician, said harness including a belt to extend around a waist of the emergency medical technician and a pair of shoulder straps extending upwardly from said belt, said harness further including a back separator panel extending between said shoulder straps, and a pair of stabilizing tabs, in which each said stabilizing tab is located on one side of said back separator panel, said stabilizing tab includes an eyelet therein, said harness further including a pair of lateral underarm support straps, wherein each said lateral underarm support strap extends between one said shoulder strap, said belt including a pair of D-ring attachments, in which each said D-ring attachment is affixed mid-lateral onto said belt, said belt further including a quick release retracting buckle, so that the emergency medical technician can easily put on and take off said harness, said harness further including a chest strap extending between said shoulder straps, and a second quick release retracting buckle on said chest strap to help the emergency medical technician easily put on and take off said harness; and b) means for securing said harness within a compartment of an ambulance, so that the emergency medical technician can safely administer continuous CPR to a patient on a stretcher in the compartment, while the patient is being transported by the ambulance, said securing means including a pair of safety lines, in which each said safety line is affixed at a first end to a wall surface in the compartment of the ambulance, and a pair of hook fasteners, in which each said hook fastener is attached to a second end of one said safety line, so that each said hook fastener can connect to one said eyelet in one said stabilizing tab.

2. A CPR safety device as recited in claim 1, wherein said securing means includes:

a) a pair of safety lines, in which each said safety line is affixed at a first end to a wall surface in the compartment of the ambulance; and b) a pair of hook fasteners, in which each said hook fastener is attached to a second end of one said safety line, so that each said hook fastener can connect to one said D-ring attachment on said belt.

* * * * *